(12) United States Patent
Berkus et al.

(10) Patent No.: US 8,983,161 B2
(45) Date of Patent: Mar. 17, 2015

(54) AUTOMATIC CORRECTION METHOD OF COUCH-BENDING IN SEQUENCE CBCT RECONSTRUCTION

(75) Inventors: Timo Berkus, Ennetbaden (CH); Katharina Quintus, Zurich (CH); Markus Oelhanfen, Rohr (CH); Patrik Kunz, Baden (CH)

(73) Assignee: Varian Medical Systems International AG, Zug (CH)

( * ) Notice: Subject to any disclaimer, the term of this patent is extended or adjusted under 35 U.S.C. 154(b) by 495 days.

(21) Appl. No.: 13/292,984

(22) Filed: Nov. 9, 2011

(65) Prior Publication Data

US 2013/0114871 A1     May 9, 2013

(51) Int. Cl.
| | |
|---|---|
| G06K 9/00 | (2006.01) |
| H05G 1/28 | (2006.01) |
| G06T 11/00 | (2006.01) |
| A61B 6/00 | (2006.01) |
| A61B 6/03 | (2006.01) |

(52) U.S. Cl.
CPC ............. *G06T 11/008* (2013.01); *A61B 6/5276* (2013.01); *A61B 6/032* (2013.01); *A61B 6/5205* (2013.01); *A61B 6/5235* (2013.01); *G06T 11/003* (2013.01)
USPC .......................................... 382/131; 378/164

(58) Field of Classification Search
None
See application file for complete search history.

(56) References Cited

U.S. PATENT DOCUMENTS

| | | | |
|---|---|---|---|
| 5,872,829 A * | 2/1999 | Wischmann et al. ......... | 378/164 |
| 6,097,833 A * | 8/2000 | Lobregt et al. ................ | 382/130 |
| 6,173,033 B1 * | 1/2001 | Klingenbeck-Regn et al. ...................... | 378/20 |
| 6,700,949 B2 * | 3/2004 | Susami et al. .................. | 378/19 |
| 6,862,335 B2 * | 3/2005 | Basu et al. ......................... | 378/4 |
| 6,885,165 B2 | 4/2005 | Henley et al. | |
| 6,895,105 B2 * | 5/2005 | Wollenweber ................ | 382/131 |
| 6,904,163 B1 * | 6/2005 | Fujimura et al. .............. | 382/131 |
| 6,928,137 B2 * | 8/2005 | Bruder et al. ..................... | 378/4 |
| 7,123,779 B2 * | 10/2006 | Beuker et al. .................. | 382/294 |
| 7,292,673 B2 * | 11/2007 | Kroner et al. ................... | 378/20 |
| 7,344,306 B2 * | 3/2008 | Hsieh et al. .................... | 378/207 |
| 7,412,027 B2 * | 8/2008 | Yakubovsky et al. ........... | 378/63 |
| 7,440,535 B2 * | 10/2008 | Netsch et al. ....................... | 378/4 |
| 7,607,833 B2 * | 10/2009 | Marzendorfer ............... | 378/209 |
| 7,697,743 B2 * | 4/2010 | Metz ............................. | 382/131 |
| 7,729,527 B2 * | 6/2010 | Maschauer et al. ........... | 382/132 |
| 7,822,251 B2 * | 10/2010 | Ding ............................. | 382/130 |

(Continued)

FOREIGN PATENT DOCUMENTS

JP            2004180846 A   *   7/2004  ............... A61B 6/03

OTHER PUBLICATIONS

Ge Wang et al., A General Cone-Beam Reconstruction Algorithm, IEEE Transactions on Medical Imaging, Sep. 1993, pp. 486-496, vol. 12, No. 3.

*Primary Examiner* — Wenpeng Chen
(74) *Attorney, Agent, or Firm* — Vista IP Law Group, LLP (57) ABSTRACT

A method for correcting a volumetric image to address error due to deflection of a patient support is provided. The method includes obtaining a first set of projection data and a second set of projection data. The first and second sets of projection data are generated when the patient is at a first position and a second position, respectively, and are usable to reconstruct a first volumetric image and a second volumetric image, respectively. A corrected volumetric image is then determined based on the first and second sets of projection data.

24 Claims, 6 Drawing Sheets

(56) References Cited

U.S. PATENT DOCUMENTS

| | | | |
|---|---|---|---|
| 7,863,574 B2 * | 1/2011 | Hahn et al. | 250/363.05 |
| 7,865,005 B2 * | 1/2011 | Ye et al. | 382/131 |
| 8,041,409 B2 * | 10/2011 | Leevy et al. | 600/407 |
| 8,086,010 B2 * | 12/2011 | Nabatame et al. | 382/131 |
| 8,107,730 B2 * | 1/2012 | Kariv | 382/182 |
| 8,218,843 B2 * | 7/2012 | Edlauer et al. | 382/131 |
| 8,511,894 B2 * | 8/2013 | Gagnon et al. | 378/205 |
| 2002/0081008 A1 * | 6/2002 | Wollenweber | 382/131 |
| 2002/0122575 A1 * | 9/2002 | Vaisburd et al. | 382/131 |
| 2002/0186819 A1 * | 12/2002 | Proksa | 378/207 |
| 2003/0058984 A1 * | 3/2003 | Susami et al. | 378/19 |
| 2004/0141581 A1 * | 7/2004 | Bruder et al. | 378/4 |
| 2004/0264625 A1 * | 12/2004 | Basu et al. | 378/4 |
| 2005/0065421 A1 * | 3/2005 | Burckhardt | 600/407 |
| 2005/0152492 A1 * | 7/2005 | Yakubovsky et al. | 378/20 |
| 2005/0245807 A1 * | 11/2005 | Boese et al. | 600/407 |
| 2006/0184012 A1 * | 8/2006 | Marzendorfer | 600/425 |
| 2007/0003020 A1 * | 1/2007 | Hsieh et al. | 378/207 |
| 2008/0117229 A1 * | 5/2008 | Wegenkittl et al. | 345/619 |
| 2008/0123924 A1 * | 5/2008 | Nabatame et al. | 382/131 |
| 2008/0125639 A1 * | 5/2008 | Ding | 600/407 |
| 2008/0292048 A1 * | 11/2008 | Haras et al. | 378/20 |
| 2009/0268875 A1 * | 10/2009 | Edlauer et al. | 378/163 |
| 2010/0034435 A1 * | 2/2010 | Kariv | 382/128 |
| 2010/0046696 A1 * | 2/2010 | Maltz | 378/7 |
| 2010/0102239 A1 * | 4/2010 | Hahn et al. | 250/363.05 |
| 2010/0215150 A1 * | 8/2010 | Vallee et al. | 378/98.12 |
| 2012/0093380 A1 * | 4/2012 | Gagnon et al. | 382/131 |
| 2013/0006036 A1 * | 1/2013 | Raleigh et al. | 600/1 |
| 2013/0114871 A1 * | 5/2013 | Berkus et al. | 382/131 |

\* cited by examiner

AUTOMATIC CORRECTION METHOD OF COUCH-BENDING IN SEQUENCE CBCT RECONSTRUCTION

FIELD

This application relates generally to radiation systems and methods, and more particularly, to radiation systems and methods that involve a moveable patient support.

BACKGROUND

Computed tomography (CT) is an imaging technique that has been widely used in the medical field. In a procedure for computed tomography, an x-ray source and a detector apparatus are positioned on opposite sides of a portion of a patient under examination. The x-ray source generates and directs an x-ray beam towards the patient, while the detector apparatus measures intensity values produced by the x-ray beam during the process. The detector apparatus produces a voltage proportional to the intensity of incident x-rays, and the voltage is read and digitized for subsequent processing in a computer. By taking a plurality of readings from multiple angles around the patient, relatively massive amounts of data are thus accumulated. The accumulated data are then analyzed and processed for reconstruction of a matrix (visual or otherwise), which constitutes a depiction of a density function of a volume of the bodily region being examined. By considering one or more sections in the volume, a skilled diagnostician can often diagnose various bodily ailments such as tumors, blood clots, etc.

In existing CT procedures, a patient support may be used to position a patient while the radiation source of the CT machine is rotated about the patient. Such patient support may have a cantilever configuration in which one end of the patient support is connected to a base, while an opposite end of the patient support is a free end. The patient support may be translated from a first position to a second position along its longitudinal axis (e.g., Z-axis) during the imaging procedure.

Applicants of the subject application determine that as the patient support is translated during an imaging procedure, the patient support may bend due to its cantilever configuration. For example, as the patient support is translated further away from its base, the cantilever section of the patient support may lengthen, resulting in an unintended vertical deflection at the free end (and other positions along the length) of the patient support. The vertical deflection may vary, depending on the cantilever length. The further the free end is away from the support base, the more the deflection. Furthermore, Applicants of the subject application determine that mechanical slippage, strains of different mechanical components, and/or the patient's weight may also contribute to unintentional deflection of the patient support. Thus, Applicants of the subject application determine that it would be desirable to have a new imaging system and method that address the above problems.

SUMMARY

In accordance with some embodiments, an imaging method includes obtaining a first set of projection data when a patient support is at a first position, wherein the first set of projection data is usable to reconstruct a first volumetric image, obtaining a second set of projection data when the patient support is at a second position, wherein the second set of projection data is usable to reconstruct a second volumetric image, and determining a corrected volumetric image using the first set of projection data and the second set of projection data to correct for deflection of the patient support.

In accordance with other embodiments, an imaging system includes a processor configured for obtaining a first set of projection data when a patient support is at a first position, wherein the first set of projection data is usable to reconstruct a first volumetric image, obtaining a second set of projection data when the patient support is at a second position, wherein the second set of projection data is usable to reconstruct a second volumetric image, and determining a corrected volumetric image using the first set of projection data and the second set of projection data to correct for deflection of the patient support.

In accordance with other embodiments, a computer product includes a set of instruction stored in a non-transitory medium, an execution of the instruction causes a process to be performed, the process comprising obtaining a first set of projection data when a patient support is at a first position, wherein the first set of projection data is usable to reconstruct a first volumetric image, obtaining a second set of projection data when the patient support is at a second position, wherein the second set of projection data is usable to reconstruct a second volumetric image, and determining a corrected volumetric image using the first set of projection data and the second set of projection data to correct for deflection of the patient support.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 1:
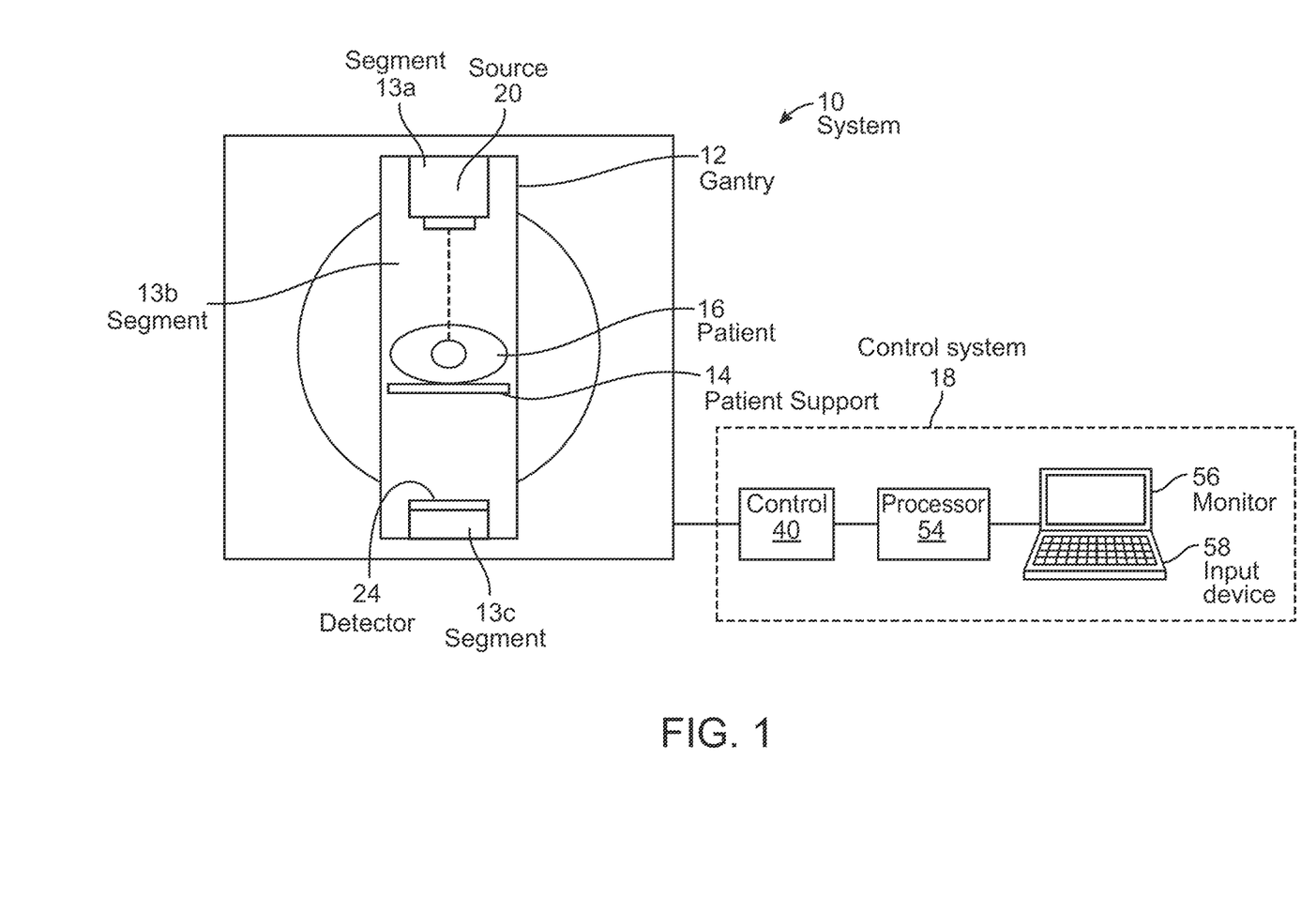
FIG. 1 illustrates a system for delivering radiation in accordance with embodiments described herein.

Referring now to the drawings, in which similar or corresponding parts are identified with the same reference numeral, FIG. 1 illustrates a computed tomography image acquisition system 10, in which embodiments of the present invention can be employed. The system 10 includes a gantry 12, a patient support 14 for positioning a patient 16, and a control system 18 for controlling an operation of the gantry 12, the patient support system 14 as well as the whole x-ray acquisition system. In the illustrated embodiments, the gantry 12 has an arm configuration (e.g., a C-arm, with segments 13a-13c forming the C-arm), such as that used in the cone beam CT machines manufactured by Varian Medical Systems, Inc., in Palo Alto, Calif. In other embodiments, instead of the arm configuration shown, the gantry 12 can have other configurations. For example, the gantry 12 can have ring configuration. The system 10 also includes an x-ray source 20 that projects a beam (e.g., a cone beam) of x-rays towards a detector 24 on an opposite side of the gantry 12 while the patient 16 is positioned at least partially between the x-ray source 20 and the detector 24. The detector 24 has a plurality of sensor elements configured for sensing an x-ray that passes through the patient 16. Each sensor element generates an electrical signal representative of an intensity of the x-ray beam as it passes through the patient 16.

In the illustrated embodiment, the control system 18 includes a processor 54, such as a computer processor, coupled to a gantry rotation control 40. The control system 18 may also include a monitor 56 for displaying data and an input device 58, such as a keyboard or a mouse, for inputting data. During a scan to acquire x-ray projection data (i.e., CT image data), the gantry 12 rotates about the patient 16. The rotation of the gantry 12 and the operation of the x-ray source 20 are controlled by the gantry rotation control 40, which provides power and timing signals to the x-ray source 20 and controls a rotational speed and position of the gantry 12 based on signals received from the processor 54. Although the control 40 is shown as a separate component from the gantry 12 and the processor 54, in alternative embodiments, the control 40 can be a part of the gantry 12 or the processor 54.

The radiation source 20 is configured to generate X-ray radiation at different photon energy levels that is between approximately 10 keV and approximately 20 MeV (or higher) in different embodiments. For example, in some embodiments, the radiation source 20 may be a diagnostic radiation source for providing diagnostic energy that is suitable for imaging. In other embodiments, the radiation source 20 can be a treatment radiation source for providing treatment energy, wherein the treatment energy may also be suitable for imaging. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 16 completely through a 360° range, or partially through a range that is less than 360°. Also, in other embodiments, the radiation source 20 is translatable relative to the patient 16. Further, the radiation source 20 is not limited to delivering diagnostic energy in the form of x-ray, and may deliver other types of radiation energy. For example, as discussed, in other embodiments, the radiation source 20 may be configured to deliver radiation beam having an energy sufficient for treating a patient.

Figure 2:
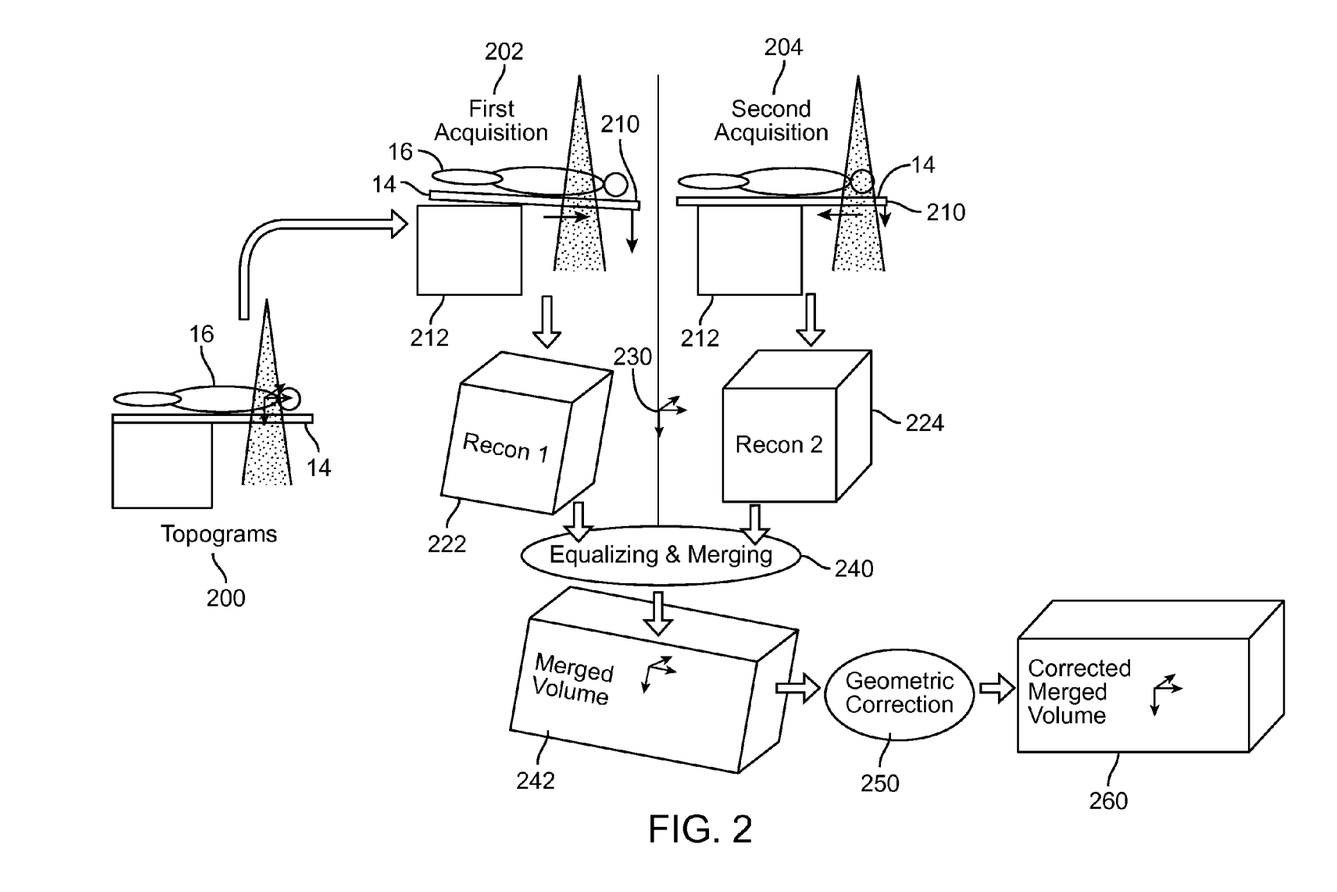
FIG. 2 illustrates a concept of couch bending correction in accordance with some embodiments.

FIG. 2 illustrates a concept of couch deflection correction in accordance with some embodiments. As used in this specification, the term "deflection" or similar terms, such as "couch deflection" refer to any movement of any part of the patient support 14 in any direction, wherein such movement may be caused by any phenomenon, including but not limited to bending of component(s) of the patient support 14, mechanical slippage of the component(s), strains of mechanical component(s), weight of component(s) of the patient support 14, and/or the weight of the patient 16 that is being supported on the patient support 14.

As shown in FIG. 2, the patient 16 is initially positioned on the patient support 14, and a topogram(s) 200 is generated. As used in this specification, the term "topogram" refers to any two-dimensional image that is generated for use as a reference/overview image. In some embodiments, one topogram may be generated that includes one two-dimensional image. In other embodiments, two topograms may be generated that include two two-dimensional images that are oriented by 90° with respect to each other. The topogram(s) 200 may be generated using the radiation source 20 and imager 24. In other embodiments, the topogram(s) 200 may be generated using other imaging devices. In the illustrated embodiments, the topogram is acquired at a desired position located between (e.g., in the middle of) two positions for volumetric acquisition, wherein the desired position may be a desired position relative to an isocenter that is selected for imaging and/or treatment. For example, the patient support may be placed at a first position for acquiring a set of image data for reconstruction of a first volumetric image, and at a second position for acquiring another set of image data for reconstruction of a second volumetric image. In such cases, the topogram may be obtained at a desired position when the patient support is anywhere (e.g., in the middle) between the first and second positions.

A first image acquisition procedure 202 is then performed when the patient support 14 is at a first position, and a second image acquisition procedure 204 is performed when the patient support 14 is at a second position. In each of the image acquisition procedures 202, 204, the radiation source 20 is rotated about the patient 16, and the imager 24 is used to generate projection data at different gantry angles.

As shown in the figure, when the patient support 14 is at the first position, one end 210 of the patient support 14 extends further away from the base 212 that supports the patient support 14. When the patient support 14 is at the second position, the end 210 of the patient support 14 is closer to the base 212 (compared to that in the first position). Due to the gravitational force, the end 210 of the patient support 14 may have a higher vertical deflection (as represented by the longer vertical arrow) when the patient support 14 is at the first position than that when the patient support 14 is at the second position. The vertical deflection of the end 210 of the support 14 may be due to bending of the support 14 (e.g., due to the weight of the patient 16 and/or the weight of the support 14), mechanical slippage of component(s) of the support 14 and/ or the base 212, and/or strain of component(s) of the support 14 and/or the base 212. In some cases, the base 212 may be considered to be a part of the patient support 14.

Although the distal end 210 of the support 14 is illustrated as being further away from the base 212 when in the first position than when in the second position, in other embodiments, the end 210 of the support 14 may be closer to the base 212 when in the first position than when in the second position.

Next, projection data from the first image acquisition procedure 202 is used to reconstruct a first volumetric image 222 (e.g., first CT image), and projection data from the second image acquisition procedure 204 is used to reconstruct a second volumetric image 224 (e.g., second CT image). As shown in the figure, the positions of the first and second volumetric images 222, 224 are with respect to a reference location 230, which may be an isocenter in some embodiment. In the illustrated example, the reference location 230 is not within each of the volumetric images 222, 224. In other examples, each or both of the volumetric images 222, 224 may include the reference location 230 (e.g., the isocenter).

Next, an equalizing and merging method 240 is performed to determine a merged volume 242. The merged volume 242 includes a first portion that is formed using the first volumetric image 222 (or projection data from the first image acquisition when the patient support 14 is at the first position), and a second portion that is formed using the second volumetric image 224 (or projection data from the second image acquisition when the patient support 14 is at the second position). In the merge volume 242, effects due to couch deflection are removed or at least partially reduced. In the illustrated embodiments, the merged volumetric image 242 is determined by combining the first and second volumetric images 222, 224 to form a combined image such that a projection of the combined image best correlates with the topogram 200. In one implementation, the relative position between the first and second volumetric images 222, 224 is adjusted until the projection of the combined image best matches with the topogram 200 (e.g., until a correlation value between the projection and the topogram reaches a prescribed threshold). The adjustment of the relative position may involve changing a distance between the two volumetric images 222, 224, and/or rotating one of the volumetric images 222, 224 relative to the other. The projection of the combined volumetric image has the same angle as that of the topogram 200. Also, in some embodiments, while merging the two volumes together, steep changes in intensity values or brightness modulation (such as those caused by the geometry of the reconstructed volume, and/or physical effects like heel effect) may be corrected in an equalizing procedure.

Next, geometric correction 250 is determined for the merged volume 242. The previous step (equalizing and merging) returns a combined image in a coordinate system where the volumes are properly combined together (relative to each other). The geometry correction is a coordinate system change to determine the position of the merged volume 242 relative to a treatment coordinate system. The new coordinate system is determined by using the correlation maximization between the topogram and forward projections of the merged volume. This is the case if forward projection is done in the same position as the topogram was acquired. This yields to the absolute knowledge of the spatial location of the merged volume. In one implementation, the corrected position of the merged volume 242 relative to a treatment coordinate system may be determined by coordinate transformation. The merged volume 242 together with the transformed coordinate (collectively, data 260) may be stored in a non-transitory medium.

Figure 3:
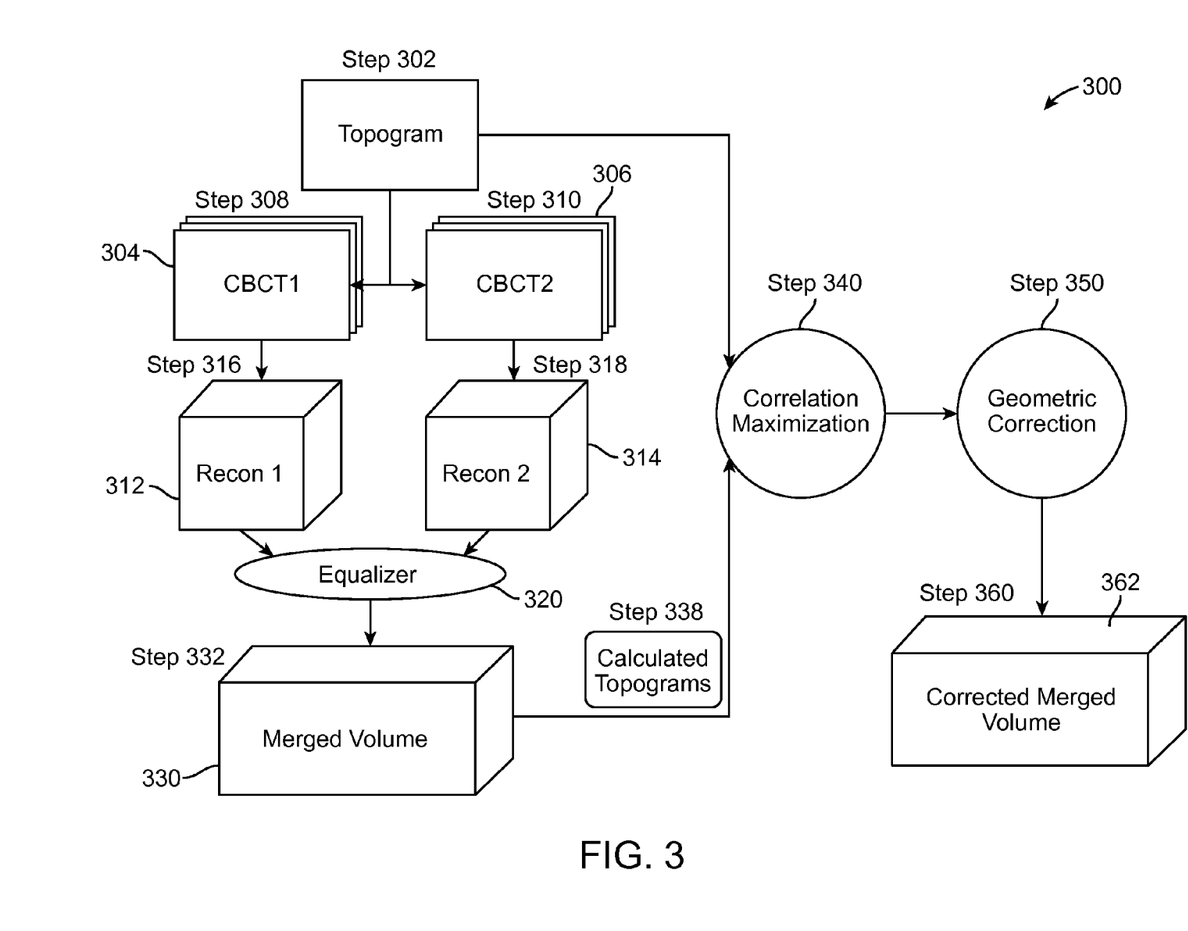
FIG. 3 illustrates a method of correcting for couch bending effect in accordance with some embodiments.

FIG. 3 illustrates a method 300 of determining a CT image that takes into account the effect of couch deflection in accordance with some embodiments. The method 300 is an implementation of the concept illustrated in FIG. 2. First one or more topograms are obtained (step 302). Such may be accomplished by obtaining two dimension low dose image(s). For example, the radiation source 20 or another radiation source may be activated to obtain at least one lateral topogram. In other embodiments, two topograms that are oriented by 90° with respect to each other may be obtained. Such may be accomplished by using two radiation sources that are 90° apart from each other, or by using one radiation source (e.g., source 20) in which the source is placed at a first position to obtain the first topogram, and then at a second position to obtain the second topogram. In further embodiments, if two topograms are obtained, they are not limited to be 90° apart, and may be apart from each other by other ranges of angles. In the illustrated embodiments, the topogram(s) is obtained at a position that is between (e.g., in the middle) two positions of respective volumetric images that are desired to be obtained. In further embodiments, the topogram(s) may be obtained using other imaging devices.

Next, a first set of cone beam CT (CBCT) data 304 and a second set of CBCT data 306 are obtained (steps 308, 310). The first and second sets of data 304, 306 are generated based on a desired scan range that is predetermined by a user before the imaging process occurs. In the illustrated embodiments, the first set 304 of CBCT data is obtained when the patient support 14 is at a first position, and the second set 306 of CBCT data is obtained when the patient support 14 is at a second position that is different from the first position. For example, in some embodiments, the patient support 14 may be placed at the first position, and the radiation source 20 is then rotated about the patient 16 to obtain projection data at different gantry angles. The patient support 14 may then be placed at the second position, and the radiation source 20 is then rotated again about the patient 16 to obtain projection data at different gantry angles. It should be understood that since the first and second sets 304, 306 of CBCT data are obtained when the patient support 14 is at different positions, the sets 304, 306 of CBCT data contain image data of different parts of the patient 16. However, in some embodiments, the sets 304, 306 may also include image data for a same part of the patient 16. Also, in the illustrated embodiments, the topogram(s) was obtained in step 302 when the patient support 14 is at a position that is between (e.g., in the middle) the first and second positions.

It should be noted that the first and second sets of data 304, 306 may be stored in a non-transitory medium for allowing them to be processed at a later time. In other embodiments, the sets 304, 306 of data may be displayed on a screen for allowing a user to study them.

Next, the first set 304 of CBCT data is used to reconstruct a first volumetric image 312, and the second set 306 of CBCT data is used to reconstruct a second volumetric image 314 (steps 316, 318). The reconstruction of the volumetric images 312, 314 may be performed by the processor 54 or another processor. Techniques for reconstructing a volumetric image using projection data are well known, and therefore, will not be described in detail. The first and second volumetric images 312, 314 may be stored in a non-transitory medium for allowing them to be processed at a later time. Additionally, or alternatively, the first volumetric image 312 and/or the second volumetric image 314 may be displayed on a screen for allowing a user to study them.

Next, the volumetric images 312, 314 are combined to form a merged volumetric image 330 (step 332). Such may be accomplished by registering the volumetric images 312, 314 relative to a common reference location/coordinate (such as the isocenter) using the topogram, and then combining the volumetric images 312, 314. When combining the two volumetric images 312, 314 to form the merged volumetric image 330, the respective positions of the volumetric images 312, 314 relative to the reference location 230 (e.g., isocenter) are maintained.

In some embodiments, the combining of the volumetric images 312, 314 may be performed using an equalizer 320. The equalizer 320 is configured to perform equalization of measured attenuation values to correct for overlaps between the sequence volumes and for potential heel effects. In particular, due to the cone beam geometry, sometime it may not be possible to reconstruct the complete range of the acquired data of one scan. To combine now two adjacent volumes, it would be desirable to acquire data in a well defined "overlap" region. Otherwise, there would appear a gap in the middle of the combined/merged volume along with severe artifacts. The "Heel Effect" is the projection of the tube-anode shape onto the projection image. This yields a linear increase of the signal in the detector in the direction the anode-table is oriented. As a result, one end of the reconstructed volume is brighter than the other. The goal of removing heel effect is to eliminate this attenuation (gray value) gradient. Overlaps may be taken into account by "blending" one image into the other (after heel effect has been corrected). In some cases, equalization of measured attenuation values may be performed to correct for the overlaps. The equalizer 320 may be implemented as a part of the processor 54 or another processor. For example, in some embodiments, the equalizer 320 may be implemented as software that is processed by the processor 54 or another processor.

The merged volume 330 may be stored in a non-transitory medium for allowing it to be processed at a later time. Additionally, or alternatively, the merged volume 330 may be displayed on a screen for allowing a user to study the volumetric image 330.

Next, one or more topograms are calculated using the merged volume 330 (step 338). For example, the topogram may be obtained by extracting a two dimensional slice (image) of the merged volume 330. In such cases, the topogram is a two dimensional projection derived from the three dimensional volume 330. The orientation of the calculated topogram corresponds with (e.g., is the same as) the orientation of the topogram obtained in step 302. In some embodiments, if a plurality of topograms is obtained in step 302, then in step 338, the processor 54 (or another processor) may calculate a plurality of topograms from the merged volume 330 that correspond with the respective topograms obtained in step 302.

Next, the calculated topograms obtained from step 338 are compared with the initial topogram(s) obtained from step 302, and a correlation between them is determined (step 340) using the processor 54 (or another processor).

In some embodiments, an iterative process may be utilized in which the steps (steps 332, 338, 340) of determining a merged volumetric image, determining a calculated topogram, and comparing the calculated topogram with the initial topogram, are repeated in order to determine a desired merged volumetric image. In such cases, the two volumetric images 312, 314 are combined, and a topogram (e.g., a projection) is calculated from the merged volume 330. Then the calculated topogram is compared with the topogram that was obtained in step 302. In some embodiments, a correlation value is determined between the calculated topogram and the measured topogram. Next, the position of the volumetric images 312, 314 is adjusted to obtain another merged volume 330, and a topogram is calculated from the merged volume 330. For example, the volumetric images 312, 314 may be translated and/or oriented relative to each other to form the merged volumetric image 330 so that the projection (with the same orientation as that of the topogram) will match the topogram. The calculated topogram of the new merged volume 330 is then compared with the initial topogram to obtain another correlation value. The above technique is repeated until a desired merged volume 330 is obtained. In some embodiments, the adjustment of the relative position between the volumetric images 312, 314 is performed to improve the correlation value between the calculated topogram and the measure topogram. When the correlation value exceeds a predetermined threshold, then the processor may determine that the merged volume 330 is the desired merged volume 330.

In other embodiments, a plurality of topograms may be calculated, that correspond with different respective relative positions between the first and second volumetric images 312, 314. In such cases, each of the calculated topograms is compared with the reference topogram determined in step 302 to obtain different respective correlation values. The processor then selects the relative position between the first and second volumetric images 312, 314 that results in the maximal correlation between the calculated topogram and the reference topogram. In one implementation, forward-projections of the combined volumetric image 330 are used to determine the maximum correlation between the calculated topogram(s) and the initial measured topogram(s). As used in this specification, the term "maximized" or similar terms such as "maximizing", "maximum", "maximal", etc., does not necessarily refer to a value having a highest value, and may refer to a value that is above a prescribed threshold.

In further embodiments, when determining the merged volumetric image 330 in step 332, the relative position between the volumetric images 312, 314 may be selected so that a projection of the merged volumetric image will best correspond with the topogram obtained in step 302.

In any of the embodiments described herein, a correlation optimization method may be used to determine a merged volume that will result in the maximum correlation between the calculated topogram and the reference topogram. For example, in one implementation, the relative positioning between the two volumetric images may be determined by an iterative approach using the maximization of the correlation function (which correlates original topograms vs. calculated topograms). In other embodiments, mutual information maximization may be used to determine a merged volume that will result in the maximum correlation between the calculated topogram and the reference topogram. In still other embodiments, the processor may determine corresponding landmarks in the calculated topogram and the reference topogram, and use the landmarks to determine a maximum correlation between the calculated topogram and the reference topogram. In further embodiments, other image registration techniques may be used to determine a merged volume that will result in the maximum correlation between the calculated topogram and the reference topogram.

As illustrated in the above embodiments, the reference topogram(s) in step 302 is used to align the first and second volumetric images 312, 314 so that the merged volume 330 will correct for the undesirable effects due to deflection of the patient support. In particular, because the reference topogram(s) is obtained when the patient support is at a single position that is between the positions of the respective volumetric images 312, 314, the reference topogram(s) provides an accurate reference showing what a projected image for a desirable merged volume (one that has compensated for deflection of the patient support) should look like. If the two volumetric images 312, 314 are combined to form a merged volume without compensating for the deflection of the patient support, the calculated topogram from such merged volume will be different from the reference topogram. This is because the deflection of the patient support will cause the two volumetric images 312, 314 (which are obtained when the patient support is at different respective positions) to tilt relative to each other, while on the other hand, the reference topogram(s) is created when the patient support is at one position (and therefore provides an accurate reference of what a calculated topogram for a desired merged volume should look like).

In the illustrated embodiments, after a desired merged volume 330 is obtained, a geometric correction is then determined (step 350), and the geometric correction is then used to change a coordinate system for the merged volume 330 so that a position of the merged volume 330 is expressed in a desired coordinate system (step 360). The previous step (equalizing and merging) returns a combined image in a coordinate system where the volumes are properly combined together (relative to each other). The geometry correction is a coordinate system change to determine the position of the merged volume relative to a treatment coordinate system. The new coordinate system is determined by using the correlation maximization between the topogram and forward projections of the merged volume. This is the case if forward projection is done in the same position as the topogram was acquired. This yields to the absolute knowledge of the spatial location of the merged volume. In one implementation, the corrected position of the merged volume 330 relative to a treatment coordinate system may be determined by coordinate transformation.

In some embodiments, the merged volume 330 along with its position relative to a treatment coordinate system (collectively, data 362) may be stored in a non-transitory medium for allowing it to be used at a later time. Additionally, or alternatively, the corrected merged volume 330 may be displayed on a screen for allowing a user to study the corrected merged volumetric image 330.

In the above embodiments, the couch bending technique does not require any prior knowledge about the mechanical properties of the patient support 14. However, in other embodiments, mechanical properties of the patient support 14 may be input into the processor 54 (or another processor) for increasing the speed, quality, and/or reliability of the couch bending correction method. For example, in other embodiments, the direction of bending of the patient support 14, and/or the range of expected movement of the patient support 14 between the first and second positions (or during the prescribed range of scan) may be input into the processor 54. Such information may be used by the processor (or another processor) to improve the efficiency in the determination of the maximum correlation between the calculated topogram(s) and the measured topogram(s), the determination of geometric correction, and the determination of the corrected volumetric image.

As shown in the above embodiments, the couch deflection correction technique is advantageous because it allows unintended deflection of the patient support 14 to be automatically corrected, wherein the unintended deflection may be due to any one or any combination of bending of component(s) of the patient support 14, mechanical slippage of the component(s), strains of mechanical component(s), weight of component(s) of the patient support 14, and the weight of the patient 16 that is being supported on the patient support 14.

Thus, embodiments of the method and system described herein allow volumetric image, such as cone beam CT image, to be accurately determined.

It should be noted that in other embodiments, one or more of the steps described in the method 300 may be combined. Also, in other embodiments, the order of the steps in the method 300 may be different from that illustrated.

Figure 4:
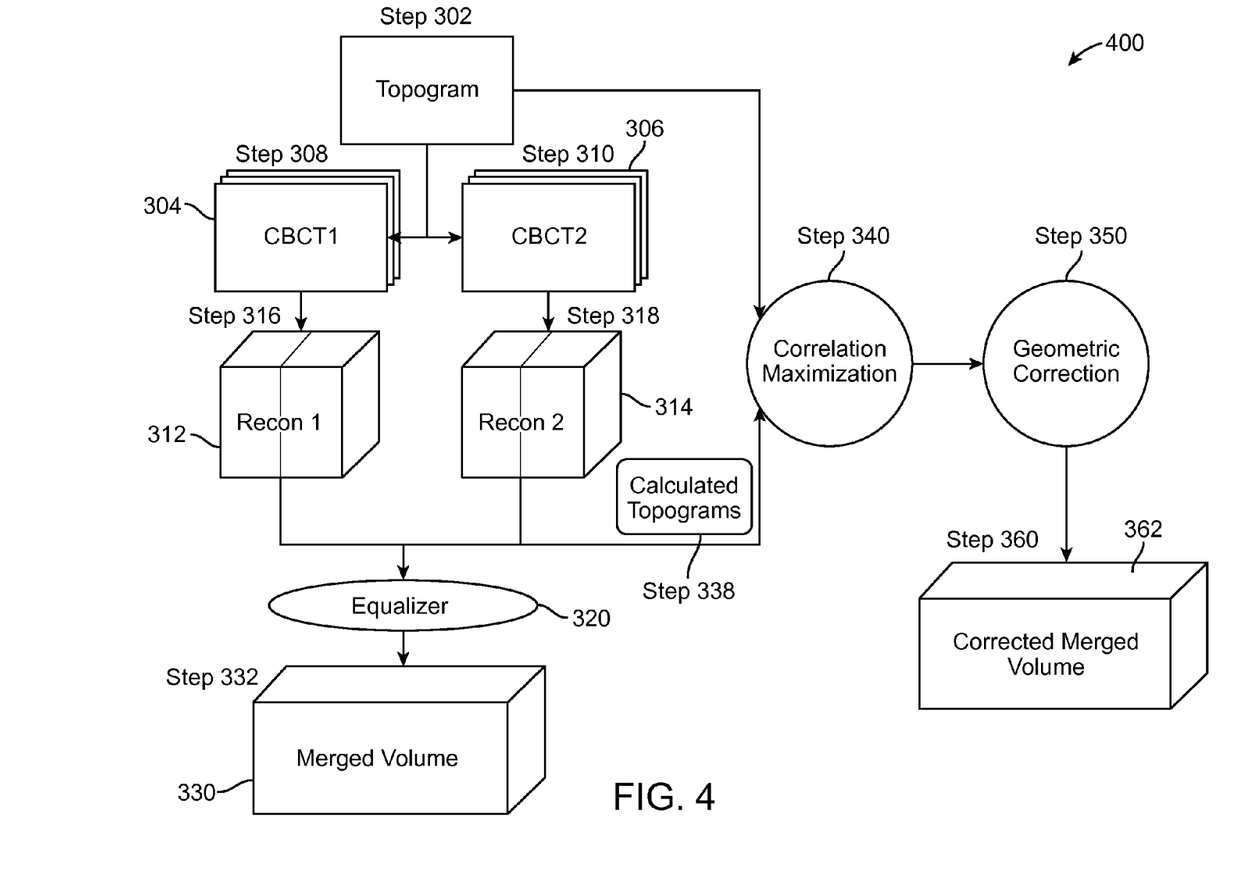
FIG. 4 illustrates another method of correcting for couch bending effect in accordance with other embodiments.

FIG. 4 illustrates another method 400 of determining a CT image (such as CBCT image) that takes into account the effect of couch deflection in accordance with other embodiments. The method 400 is the same as the method 300, except that the merged volume 330 is not needed before the topogram(s) in step 338 is determined. Instead, as shown in the figure, the first and second reconstructed volumetric images 312, 314 (instead of the merged volume 330) may be used to calculate the topogram(s) (step 338). For example, in some embodiments, the topogram may be obtained by taking a two dimensional slice from the first volumetric image 312, taking a two dimensional slice from the second volumetric image 314, and combining them. In such technique, the orientations of the two dimensional slices from the two volumetric images 312, 314 correspond with (e.g., are the same as) the orientation of the topogram obtained in step 302. Also, when combining the two slices to form the calculated topogram in step 338, the respective positions of the slices relative to the reference location 230 (e.g., isocenter) are maintained, such that the two slices are correctly positioned relative to each other.

It should be noted that in any of the embodiments described herein, one or more steps may be combined. Also, in any of the embodiments described herein, any of the steps may be further divided into substeps. Furthermore, the order of the steps described herein may be different in other embodiments.

Figure 5:
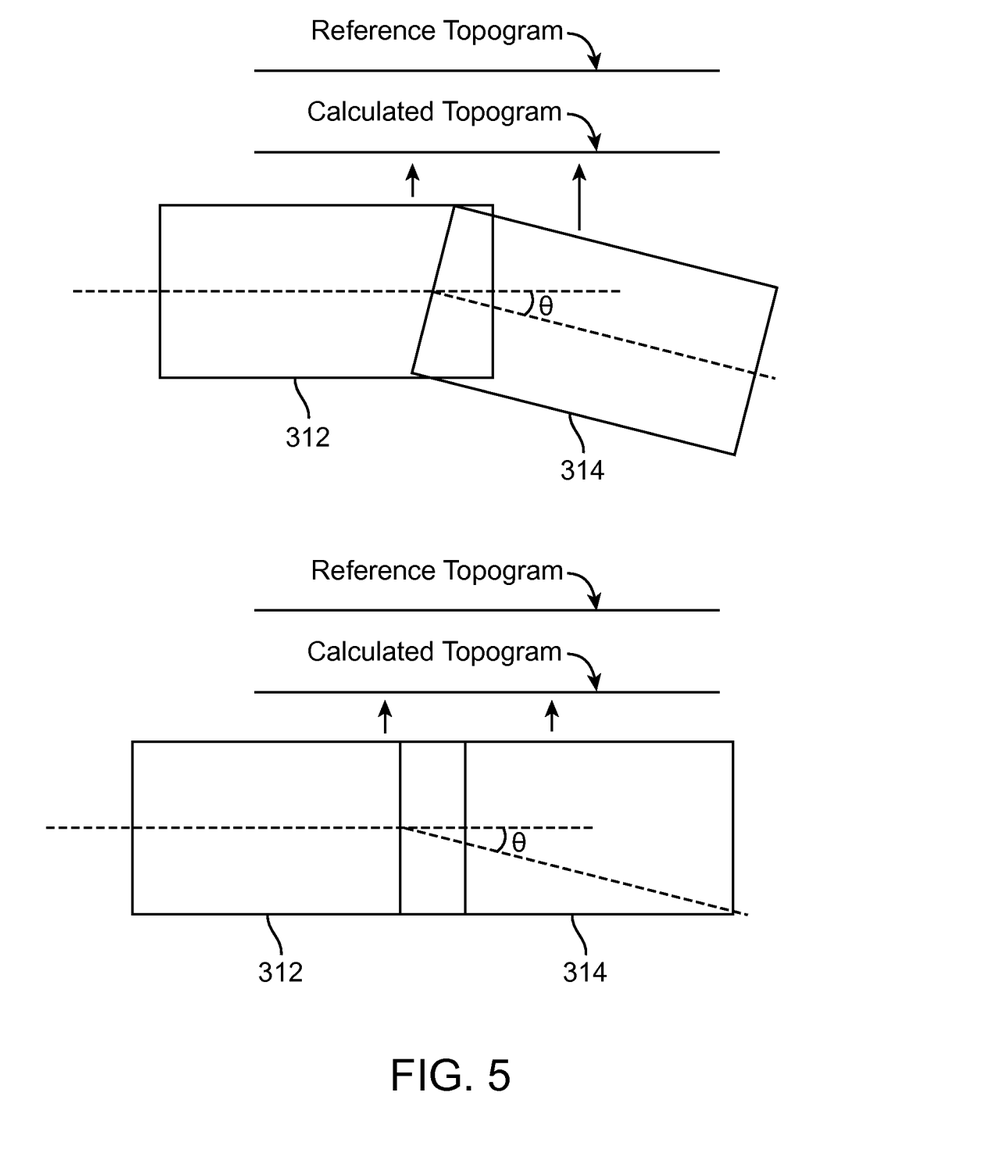
FIG. 5 illustrates a concept of correction for couch bending effect in accordance with some embodiments.

FIG. 5 illustrates the concept of correction for couch bending effect in accordance with some embodiments. As shown in the top part of the figure, due to deflection of the patient support 14, the two volumetric images 312, 314 may be tilted by an angle θ relative to each other. As a result, the calculated topogram, which is a two dimensional projection derived from portions of the respective volumetric images 312, 314, may not best correlate with the reference topogram. Embodiments of the technique described herein allow the relative positioning of the volumetric images 312, 314 to be adjusted to compensate for the tilting angle due to deflection of the support 14. As shown in the bottom part of the figure, by determining a calculated topogram that matches the reference topogram, the processor can determine the relative tilting between the two volumetric images 312, 314 to correct for couch bending effect.

Computer System Architecture

Figure 6:
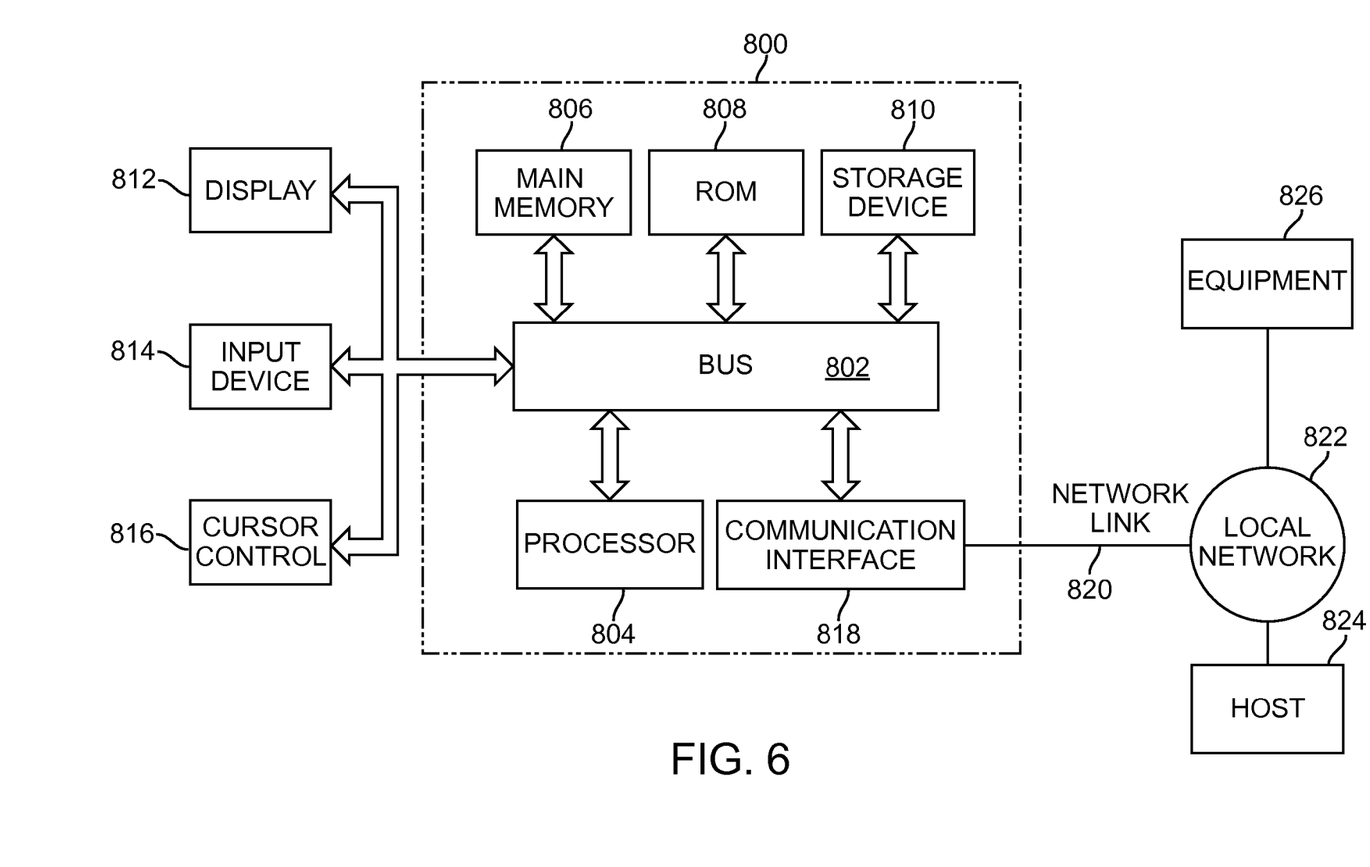
FIG. 6 is a block diagram of a computer system architecture, with which embodiments described herein may be implemented.

FIG. 6 is a block diagram that illustrates an embodiment of a computer system 800 upon which an embodiment of the invention may be implemented. Computer system 800 includes a bus 802 or other communication mechanism for communicating information, and a processor 804 coupled with the bus 802 for processing information. The processor 804 may be an example of the processor 54 of FIG. 1, or another processor that is used to perform various functions described herein. In some cases, the computer system 800 may be used to implement the processor 54. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 812, such as a cathode ray tube (CRT) or a flat panel, for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

The computer system 800 may be used for performing various functions (e.g., calculation) in accordance with the embodiments described herein. According to one embodiment, such use is provided by computer system 800 in response to processor 804 executing one or more sequences of one or more instructions contained in the main memory 806. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. A non-volatile medium is an example of a non-transitory medium. Volatile media includes dynamic memory, such as the main memory 806. A volatile medium is another example of a non-transitory medium. In some embodiments, the non-transitory medium may be used to store any information that is involved in the embodiments of the method described herein. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826 such as a radiation beam source or a switch operatively coupled to a radiation beam source. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although the embodiments of the systems and methods have been described with reference to generating CT or CBCT images, it should be understood that the systems and methods may also be implemented in different medical procedures, such as in a treatment procedure (which may involve use of a treatment radiation beam emitted from a treatment radiation source). In addition, although the gantry 12 has been described as making a 360° rotation around the patient 16 during CT image data acquisition, such needs not be the case. For example, if a full cone detector is used, the system 10 may acquire data while the gantry 12 rotates 180° plus the angle of the beam pattern. Other angles of rotation may also be used, depending on the particular system being employed and the particular need of an application. For example, in some procedures, it may be desirable to obtain image data (which may, for example, be incomplete for the purpose of performing 3D reconstruction) at certain prescribed of gantry angle(s). Furthermore, instead of a CT procedure, the above described techniques can be implemented in a MRI procedure, a PET procedure, or other imaging procedures, in which a plurality of image data is desired to be generated. As such, the gantry should not be limited to a rotatable structure as described previously, and could have other configurations, such as a sliding or translating configuration, depending on the particular application or procedure.

Furthermore, although the above embodiments have been described as involving two sets of CT (e.g., CBCT) acquisitions, in other embodiments, more than two sets of CT image data may be obtained in respective positions. For example, in some embodiments, three sets of CT image data may be obtained in three different respective positions along a longitudinal axis of a patient support. In such cases, the three sets of CT image data may be used by the processor to reconstruct three different respective volumetric images. The first and second volumetric images will have a first overlapping region, and the second and third volumetric images will have a second overlapping region. In some embodiments, a topogram may be obtained that covers the image range of all three volumetric images. The processor then uses the topogram to align the first and second volumetric images so that a relative deflection of the patient support between the first and second positions (for the respective first and second volumetric images) is compensated. The processor also uses the same topogram to align the second and third volumetric images so that a relative deflection of the patient support between the second and third positions (for the respective second and third volumetric images) is compensated. For example, any of the image registration techniques described herein may be used to align the first and second volumetric images so that their respective projections match the topogram (e.g., a first portion of the topogram), and to align the second and third volumetric images so that their respective projections match the same topogram (e.g., a second portion of the topogram).

In other embodiments, a first topogram may be obtained that covers the image range of the first volumetric image and at least a portion of the second volumetric image, and a second topogram may be obtained that covers the image range of the third image and at least a portion of the second volumetric image. In such cases, the processor is configured to use the first topogram to align the first and second volumetric images so that a relative deflection of the patient support between the first and second positions (for the respective first and second volumetric images) is compensated. The processor is also configured to use the second topogram to align the second and third volumetric images so that a relative deflection of the patient support between the second and third positions (for the respective second and third volumetric images) is compensated. For example, any of the image registration techniques described herein may be used to align the first and second volumetric images so that their respective projections match the first topogram, and to align the second and third volumetric images so that their respective projections match the second topogram.

Although particular embodiments have been shown and described, it will be understood that they are not intended to limit the present inventions, and it will be obvious to those skilled in the art that various changes and modifications may be made without departing from the spirit and scope of the present inventions. For example, as used in this specification, the term "image" or "image data" does not necessarily refer to image or image data that is displayed, and may refer to image or image data that is stored in a computer-readable medium, such as a non-transitory medium. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. An imaging method, comprising:
    obtaining a first set of projection data, wherein the first set of projection data is generated when a patient support is at a first position;
    obtaining a second set of projection data, wherein the second set of projection data is generated when the patient support is at a second position;
    obtaining a topogram;
    determining a first volumetric image using the first set of projection data;
    determining a second volumetric image using the second set of projection data; and
    determining a corrected volumetric image based on the topogram, the first volumetric image that is determined using the first set of projection data, and the second volumetric image that is determined using the second set of projection data, to correct for deflection of the patient support.

2. The method of claim 1, wherein the act of determining the corrected volumetric image comprises combining the first and second volumetric images to form a combined image such that a projection of the combined image best correlates with the topogram.

3. The method of claim 1, wherein the topogram is created when the patient support is at a third position that is different from the first and second positions.

4. The method of claim 1, wherein the deflection of the patient support corrected in the corrected volumetric image is due to bending of a component of the patient support.

5. The method of claim 1, wherein the deflection of the patient support corrected in the corrected volumetric image is due to mechanical slippage of a component of the patient support.

6. The method of claim 1, wherein the deflection of the patient support corrected in the corrected volumetric image is due to one or both of a weight of a component of the patient support, and a weight of a patient being supported on the patient support.

7. The method of claim 1, further comprising determining a geometric correction for the corrected volumetric image.

8. The method of claim 1, further comprising removing a brightness modulation caused by a physical effect in the corrected volumetric image.

9. An imaging system, comprising:
    a medium storing a first set of projection data; and
    a processor communicatively coupled to the medium, the processor configured for:
        obtaining the first set of projection data from the medium, wherein the first set of projection data is generated when a patient support is at a first position;
        obtaining a second set of projection data, wherein the second set of projection data is generated when the patient support is at a second position;
        obtaining a topogram;
        determining a first volumetric image using the first set of projection data;
        determining a second volumetric image using the second set of projection data; and
        determining a corrected volumetric image using the topogram, the first volumetric image that is determined using the first set of projection data, and the second volumetric image that is determined using the second set of projection data, to correct for deflection of the patient support.

10. The imaging system of claim 9, wherein the processor is configured for determining the corrected volumetric image by combining the first and second volumetric images to form a combined image such that a projection of the combined image best correlates with the topogram.

11. The imaging system of claim 9, wherein the topogram is created when the patient support is at a third position that is different from the first and second positions.

12. The imaging system of claim 9, wherein the deflection of the patient support corrected in the corrected volumetric image is due to bending of a component of the patient support.

13. The imaging system of claim 9, wherein the deflection of the patient support corrected in the corrected volumetric image is due to mechanical slippage of a component of the patient support.

14. The imaging system of claim 9, wherein the deflection of the patient support corrected in the corrected volumetric image is due to one or both of a weight of a component of the patient support, and a weight of a patient being supported on the patient support.

15. The imaging system of claim 9, wherein the processor is configured for determining a geometric correction for the corrected volumetric image.

16. The imaging system of claim 9, wherein the processor is further configured for removing a brightness modulation caused by a physical effect in the corrected volumetric image.

17. A computer product having a set of instruction stored in a non-transitory medium, an execution of the instruction causes a process to be performed, the process comprising:
    obtaining a first set of projection data, wherein the first set of projection data is generated when a patient support is at a first position;
    obtaining a second set of projection data, wherein the second set of projection data is generated when the patient support is at a second position;
    obtaining a topogram;
    determining a first volumetric image using the first set of projection data; and
    determining a second volumetric image using the second set of projection data; and
    determining a corrected volumetric image based on the topogram, the first volumetric image that is determined using the first set of projection data, and the second volumetric image that is determined using the second set of projection data, to correct for deflection of the patient support.

18. The computer product of claim 17, wherein the act of determining the corrected volumetric image comprises combining the first and second volumetric images to form a combined image such that a projection of the combined image best correlates with the topogram.

19. The computer product of claim 17, wherein the topogram is created when the patient support is at a third position that is different from the first and second positions.

20. The computer product of claim 17, wherein the deflection of the patient support corrected in the corrected volumetric image is due to bending of a component of the patient support.

21. The computer product of claim 17, wherein the deflection of the patient support corrected in the corrected volumetric image is due to mechanical slippage of a component of the patient support.

22. The computer product of claim 17, wherein the deflection of the patient support corrected in the corrected volumetric image is due to one or both of a weight of a component of the patient support, and a weight of a patient being supported on the patient support.

23. The computer product of claim 17, wherein the process further comprises determining a geometric correction for the corrected volumetric image.

24. The computer product of claim 17, wherein the process further comprises removing a brightness modulation caused by a physical effect in the corrected volumetric image.

* * * * *